United States Patent [19]

Müller

[11] 4,124,358

[45] Nov. 7, 1978

[54] SAMPLE-INJECTION DEVICE FOR PROCESS GAS CHROMATOGRAPHY WITH CAPILLARY COLUMNS

[75] Inventor: Friedhelm Müller, Linkenheim-Hochstetten, Fed. Rep. of Germany

[73] Assignee: Siemens Aktiengesellschaft, Berlin and Munich, Fed. Rep. of Germany

[21] Appl. No.: 789,459

[22] Filed: Apr. 21, 1977

[30] Foreign Application Priority Data

May 11, 1976 [DE] Fed. Rep. of Germany ....... 2620756

[51] Int. Cl.² .............................................. B01D 15/08
[52] U.S. Cl. .......................................... 55/67; 55/197; 55/386; 73/61.1 C
[58] Field of Search ........................... 55/67, 197, 386; 73/23.1, 422 GC

[56] References Cited

U.S. PATENT DOCUMENTS

| 3,041,869 | 7/1962 | Spracklen et al. | 55/386 X |
| 3,513,636 | 5/1970 | Halasz et al. | 55/197 |
| 3,887,345 | 6/1975 | Pollock | 55/386 |
| 4,035,168 | 7/1977 | Jennings | 55/197 X |

*Primary Examiner*—John Adee
*Attorney, Agent, or Firm*—Kenyon & Kenyon, Reilly, Carr & Chapin

[57] ABSTRACT

A sample injection device for gas chromatography with a heated evaporation chamber and an adjoining split chamber for splitting the flow, in which carrier gas is introduced into the evaporation chamber and into the split chamber through respective valves. Up until the evaporation of the sample, carrier gas is conducted only into the split chamber and after evaporation, only into the evaporation chamber giving a chromatography process using capillary columns which operates with very small amounts of sample.

8 Claims, 1 Drawing Figure

U.S. Patent
Nov. 7, 1978
4,124,358
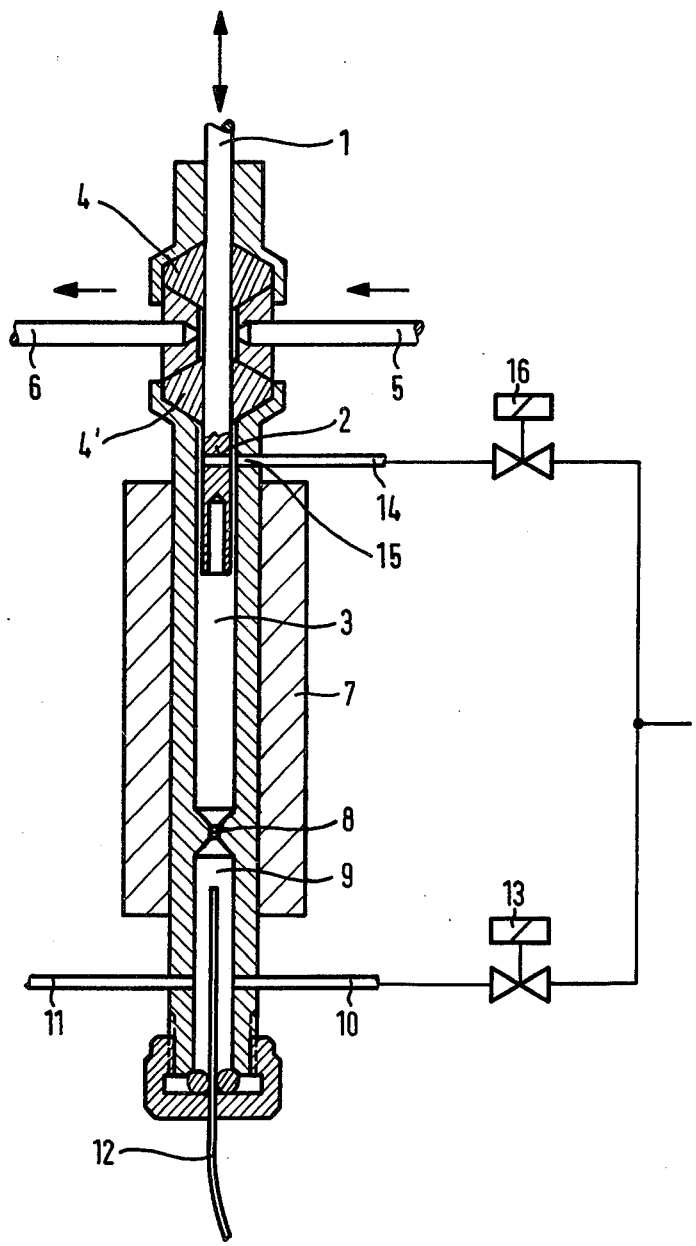

SAMPLE-INJECTION DEVICE FOR PROCESS GAS CHROMATOGRAPHY WITH CAPILLARY COLUMNS

BACKGROUND OF THE INVENTION

This invention relates to gas chromatography in general and more particularly to an improved sample injection device for process gas chromatography with capillary columns, using a heated evaporation chamber which receives the sample and from which the sample is flushed into the column via a split chamber.

In a known sample injection device, which, however, is not usable with capillary columns, the sample, dissolved in a solvent, is introduced into an evaporation chamber which can be heated. Carrier gas is fed to evaporation chamber which is initially not heated, and to the separation column via a T-shaped tubing branch. A choke is disposed in the feed line to the evaporation chamber. The carrier gas flowing via the choke into the evaporation chamber carriers the solvent away via an outlet opening of the evaporation chamber. After the solvent is evaporated, the outlet opening is closed. The carrier gas is additionally and immediately conducted into the evaporation chamber via a direct path, and the evaporation chamber is heated. In this process, the sample is flushed from the evaporation chamber into separation column via the T-shaped tubing branch. The connection of the evaporation chamber with the carrier gas via the T-shaped tubing branch and the choke is always maintained.

In this sample injection device which is described in U.S. Pat. No. 3,887,345, the solvent is distilled off before the sample is injected, in order to protect the separation column against overloading. In the process, portions of the sample to be analyzed evaporate along with the solvent, so that a reproducible measuring result is not obtained if the composition of the sample changes. Furthermore, the injection process itself takes place over such a long period of time that the injection can be applied only to packed columns.

In comparison to packed columns such as are commonly used in process chromatography, capillary columns have considerably more separating capacity. In a normal column, a time of about 20 minutes is required, for instance, for the complete separation of the components ethyl benzene/o-xylol/m-xylol/p-xylol. If a capillary column is used for this separation problem, the analysis time can be shortened by about a factor of 5 to 10. Chromatographs with such short analysis times are needed for the direct control of plants in process technology.

In order that the capacity of the capillary column can be utilized, the sample injection must be completed in a very short time. The width of many peaks is between 1 and 2 seconds in the case of capillary columns. This means that a time of less than 1 second is available for the sample injection, since the injection time adds to the peak width produced in the separation column. Such short injection times can be achieved only with dosing injectors which work with forced discharge and very small dose volumes (0.1 $\mu$l). If the sample is injected with an injector (syringe), a septum is pierced for each dosing operation. The life of such a system is limited to maximally about 200 injections because of the limited durability of the septum.

For sample injection in the case of capillary columns, very small amounts of sample, less than 0.1 $\mu$l, must be branched off, since the loading capacity of the capillary columns is extremely small. For obtaining the extremely small amount of sample, the use of a split is known. Thereby, the injected sample is divided up after the evaporation, for instance, in such a manner that of 100 parts of the sample, one part is conducted to the separation column and 99 part are diverted. In the conventional mode of operation, the carrier gas continues to flow during the evaporation process, whereby a segregation of the sample components of different boiling ranges occurs. The high boiling point components flow preferentially along the wall of the evaporation chamber, while the low boiling point ones advance in the middle with higher flow velocity. Since the inlet of the capillary column is also located in the center of the evaporation chamber, the sample composition prevailing there no longer corresponds to the composition of the injected liquid sample.

SUMMARY OF THE INVENTION

It is an object of the present invention to avoid the disadvantages of the known sample injection device described above, particularly the relatively slow sample input to the separation column, which takes place during the evaporation process, and the detrimental effect of the carrier gas flow during the evaporation process. The present invention is based on an injection device in which an evaporation chamber is separated from a chamber containing the split (split chamber) by an aperture. The separation column then immediately follows the split chamber.

According to the present invention, the evaporation chamber is connected to the carrier gas source via a first valve and the split chamber to the source via a second valve, by means of respective connecting lines. For operating the sample injection device, the procedure according to the present invention is to close the first valve until the sample is introduced and evaporated while keeping the second valve open, and to then open, after the evaporation is completed, the first valve for the injection of the sample and close the second valve.

The sample is therefore injected in two stages. In the first stage, the sample is placed in the evaporation chamber by means of a dosing device commonly used in process chromatography. The evaporation chamber is at the carrier gas pressure and its volume is designed so that the sample which is gaseous after the evaporation, can be taken up. The volume of the evaporation chamber must therefore be slightly larger than the volume of the evaporated sample under the pressure and temperature conditions prevailing in the evaporation chamber. The walls of the evaporation chamber are heated in the usual manner, so that the evaporation process can initially proceed completely separated from the sample injection. During the evaporation, no carrier gas is fed to the evaporation chamber, but the capillary column is supplied with carrier gas via the split chamber. Only after the sample is completely evaporated is the injection process itself initiated in a second step. By switching the valves, the carrier gas stream is conducted into the evaporation chamber and at the same time, the flow of carrier gas to the split chamber is interrupted. The evaporated sample, which now forms a homogeneous mixture because the flow is lacking and the temperature distribution in the evaporation chamber is constant, is thereby transferred from the evaporation chamber into the capillary column in a short time far less than 1 second.

BRIEF DESCRIPTION OF THE DRAWING

The single FIGURE is a cross section through an embodiment of a sample injection device according to the present invention.

DETAILED DESCRIPTION OF THE INVENTION

In the upper part of the drawing, the dosing plunger 1 of a dosing system commonly used in process chromatography is shown. In the positon shown on the drawing, plunger 1 is in its lower end position, where the transversal gap 2 containing the sample is inserted into the upper part of the evaporation chamber 3. The plunger is guided inside seals 4 and 4' and is moved between its upper and the lower end positions by means of a pneumatically controlled piston, not shown. In the upper end position, the transversal gap 2 is situated in the sample stream which is fed in via the connection 5 and is carried away via the connection 6. The evaporation chamber 3 is surrounded by a heater winding 7 and merges into a nozzle shaped opening 8 at its lower part. The diameter of nozzle shaped opening 8 is kept as small as possible from a manufacturing point of view and, in the present embodiment, is about 30% of the diameter of the evaporation chamber 3. Below the nozzle shaped opening 8 there is a split chamber 9. The ratio of the flow resistance of the split path through an outlet 11 and through a separation column 12 is chosen so that the desired splitting of the injected sample is achieved. Carrier gas feed lines 10 and 14 are provided coupled respectively to chambers 9 and 3 by shut off valves 13 and 16, so that carrier gas can flow in at both points.

The device shown in the drawing is operated as follows: The dosing plunger 1 is at first in its upper end position and the sample liquid flows via the lines 5 and 6 through the dosing gap 2. The evaporation chamber 3 is heated via the heater winding 7. The heating system is connected continuously. Carrier gas is conducted via the valve 13 into the split chamber, is split up in accordance with the flow resistances, and flows via the capillary column 12 to the detector (not shown) and via the line 11 to the outside. The flow of carrier gas via the feed line 14 to the entrance point 15 is shut off. Next, the dosing plunger is moved into its lower end position and the sample in the transversal gap 2 is thereby introduced into the evaporation chamber 3. The evaporation takes place in known manner. The time for the evaporation is adapted to the sample to be examined; it may be on the order of 10 to 20 seconds. Due to the small, nozzle shaped opening 8, there is practically no disturbing diffusion of the evaporated sample through the nozzle to the split chamber.

After the evaporation, the carrier gas flow via the line 10 is shut off by valve 13 and the valve 16 in the carrier gas feed line to the evaporation chamber is opened. The evaporated sample is thus transported in a time of less than 1 second from the evaporation chamber, through the nozzle shaped opening 8 and the split chamber 9, to the capillary column 12.

What is claimed is:

1. In a sample injection device for process gas chromatography with capillary columns, using a heated evaporation chamber which receives the sample and from which the sample enters the column via a split chamber, and including a narrow, nozzle shaped opening separating the evaporation chamber from the split chamber and a carrier gas source, the improvement comprising:

a. a first valve for connecting said carrier gas source to said evaporation chamber; and
 b. a second valve for connecting said carrier gas source to said split chamber, whereby said second valve may be open and said first valve closed during evaporation of the sample in the evaporation chamber whereafter said first valve can be opened and said second valve closed to transport evaporated sample to said split chamber thereby injecting it into the capillary column.

2. The improvement according to claim 1, wherein the volume of said evaporation chamber is slightly larger than the volume of the sample after evaporation under the pressure and temperature conditions prevailing in the evaporation chamber.

3. The improvement according to claim 2, wherein said evaporation chamber is tubular and the diameter of said nozzle shaped opening is about 30% of the diameter of said tubular evaporation chamber.

4. The improvement according to claim 3, wherein the inlet of the carrier gas to the evaporation chamber is disposed at the end thereof facing away from said nozzle shaped opening.

5. The improvement according to claim 1, wherein said evaporation chamber is tubular and the diameter of said nozzle shaped opening is about 30% of the diameter of said tubular evaporation chamber.

6. The improvement according to claim 2 wherein the inlet of the carrier gas to the evaporation chamber is disposed at the end thereof facing away from said nozzle shaped opening.

7. An improved sample injection method for use in a sample injection device for process gas chromatography with capillary columns using a heated evaporation chamber which receives the sample and from which the sample enters the column via a split chamber comprising:

a. separating the evaporation chamber from the split chamber with a narrow, nozzle shaped opening;
 b. establishing a flow of carrier gas into and through the split chamber;
 c. introducing the sample into the evaporation chamber and evaporating it without any gas flow through said chamber;
 d. after evaporation establishing a carrier gas flow through said evaporation chamber and said narrow nozzle shaped opening into said split chamber while at the same time terminating the flow into and through said split chamber whereby the evaporated sample will be transported from the evaporation chamber through the nozzle shaped opening and the split chamber into a capillary column in less than 1 second.

8. In a sample injection device for process gas chromatography with capillary columns, using a heated evaporation chamber which receives the sample and from which the sample enters the column via a split chamber, the evaporation chamber and split chamber being separated by an opening and said device including a carrier gas source, an improved method of supplying the sample to the capillary columns comprising:

a. providing a first valve for coupling carrier gas into the evaporation chamber and a second valve for connecting carrier gas to the split chamber;
 b. opening said second valve to the split chamber with said first valve closed and introducing and evaporaing the sample in the evaporation chamber; and
 c. closing said second valve and opening said first valve after completion of evaporation to introduce the sample into the capillary columns.

* * * * *